US008519207B2

(12) United States Patent
Armbruester et al.

(10) Patent No.: US 8,519,207 B2
(45) Date of Patent: Aug. 27, 2013

(54) USE OF A MIXTURE OF AN ORDERED INTERMETALLIC COMPOUND AND AN INERT MATERIAL AS A CATALYST AND CORRESPONDING HYDROGENATION PROCESSES

(75) Inventors: Marc Armbruester, Dresden (DE); Marcus Schmidt, Berlin (DE); Kirill Kovnir, Dresden (DE); Matthias Friedrich, Marienberg (DE); Karina Weinhold, Weissenborn-Berthelsdorf (DE); Juri Grin, Dresden (DE); Robert Schloegl, Berlin (DE)

(73) Assignee: Max-Planck-Gesellschaft zur Förderung der Wissenschaften E.V., München (DE)

( * ) Notice: Subject to any disclaimer, the term of this patent is extended or adjusted under 35 U.S.C. 154(b) by 466 days.

(21) Appl. No.: 12/678,774

(22) PCT Filed: Sep. 18, 2008

(86) PCT No.: PCT/EP2008/062424
§ 371 (c)(1),
(2), (4) Date: Jun. 18, 2010

(87) PCT Pub. No.: WO2009/037301
PCT Pub. Date: Mar. 26, 2009

(65) Prior Publication Data
US 2010/0280295 A1    Nov. 4, 2010

(30) Foreign Application Priority Data

Sep. 19, 2007    (EP) ..................................... 07018368

(51) Int. Cl.
*C07C 5/08*    (2006.01)
*C07C 5/02*    (2006.01)
*C07C 5/05*    (2006.01)
*C07C 5/09*    (2006.01)
*B01J 23/62*    (2006.01)

(52) U.S. Cl.
CPC .... *C07C 5/02* (2013.01); *C07C 5/05* (2013.01); *C07C 5/09* (2013.01); *C07C 2523/62* (2013.01)
USPC ........... 585/259; 502/300; 502/325; 502/332; 502/333; 585/250; 585/258; 585/260; 585/271; 585/275; 585/277

(58) Field of Classification Search
USPC ................. 585/250, 258, 259, 260, 271, 275, 585/277; 502/300, 325, 332, 333
See application file for complete search history.

(56) References Cited

U.S. PATENT DOCUMENTS 2,384,501 A * 9/1945 Streicher ........................ 502/301
3,759,823 A * 9/1973 Davies et al. .................. 208/138
(Continued)

FOREIGN PATENT DOCUMENTS
EP         1834939 A1    9/2007

OTHER PUBLICATIONS

Pt-Sn Phase Diagram in "PT Binary Alloy Phase Diagrams" in Alloy Phase Diagrams, vol. 3, ASM Handbook, 1992—month unknown.*

(Continued)

*Primary Examiner* — In Suk Bullock
*Assistant Examiner* — Bradley Etherton
(74) *Attorney, Agent, or Firm* — Harness, Dickey & Pierce, P.L.C.

(57) ABSTRACT

The present invention relates to a process for the hydrogenation, in particular selective hydrogenation of at least one unsaturated hydrocarbon compound comprising reacting the at least one unsaturated hydrocarbon compound with hydrogen in the presence of a hydrogenation catalyst, wherein the hydrogenation catalyst comprises a mixture of an ordered intermetallic compound and an inert material. According to another aspect, the present invention is concerned with the use of a mixture of at least one ordered intermetallic compound and at least one inert material, as a catalyst. The mixtures for use as a catalyst in the present invention can be prepared easily and achieve a superior activity in relation to the prior art, while preserving the high selectivity to the target compounds, e.g. in the selective hydrogenation of acetylene to ethylene.

14 Claims, 4 Drawing Sheets

(56) References Cited

U.S. PATENT DOCUMENTS

| | | | | |
|---|---|---|---|---|
| 4,132,673 A | * | 1/1979 | Yamaguchi | 502/333 |
| 4,507,401 A | * | 3/1985 | Dubois et al. | 502/242 |
| 5,364,998 A | * | 11/1994 | Sarrazin et al. | 585/259 |
| 5,559,065 A | * | 9/1996 | Lauth et al. | 502/5 |

OTHER PUBLICATIONS

Leofanti, et al., "Surface Area and Pore Texture of Catalysts" in Catalysis Today, 41 (1998) 207-219—month unknown.*

Ga-Pd Phase Diagram in "Ga Binary Alloy Phase Diagrams" in Alloy Phase Diagrams, vol. 3, ASM Handbook, 1992—month unknown.*

Komatsu, et al., "Catalytic Properties of Pt-Ge Intermetallic Compounds in the Hydrogenation of 1,3-Butadiene" in J. Phys. Chem. B, 1997, 101, 5565-5572—month unknown.*

"Palladium, palladium-tin, and palladium-silver catalysts in the selective hydrogenation of hexadienes: TRP, moessbauer, and infrared studies of adsorbed CO"; Journal of Catalysis, Academic Press, Duluth, MN; vol. 195. No. 1; Oct. 1, 2000, p. 88-95.

"Liquid-phase selective hydrogenation of hexa-1, 5-diene and hexa-1, 3-diene on paladium catalysts. Effect of time and silver addition", Journal of Catalysis, Academic Press, Duluth, MN; vol. 195,No. 1; Oct. 1, 2000, p. 96-105.

"Bimetallic palladium catalysts: influence of the co-metal on the catalyst performance", Journal of Molecular Catalysis A: Chemical, Elsevier, Amsterdam, NL; vol. 173, 2001, p. 117-134.

"Supported platinum-gallium catalysts for selective hydrodechlorination of CCl4", Journal of Molecular Catalysis A: Chemical, Elsevier, Amsterdam, NL, vol. 242, No. 1-2, Dec. 1, 2005, p. 119-128.

* cited by examiner

PdGa

Pd$_3$Ga$_7$

US 8,519,207 B2

USE OF A MIXTURE OF AN ORDERED INTERMETALLIC COMPOUND AND AN INERT MATERIAL AS A CATALYST AND CORRESPONDING HYDROGENATION PROCESSES

FIELD

The present invention relates to a process for the hydrogenation, preferably selective hydrogenation of unsaturated hydrocarbon compounds using a hydrogenation catalyst comprising a mixture of an inert material and an ordered intermetallic compound, as well as to the use of a corresponding mixture as a catalyst.

BACKGROUND

Selective hydrogenations of unsaturated hydrocarbon compounds are of high industrial significance. The pyrolysis of naphtha for the production of ethene, propene, butanes, 1,3-butadiene and aromatics is a key process in the modern petrochemical industry. For the nearly complete removal of alkynic compounds from the C2, C3 and C4 cuts, selective hydrogenations are generally used.

For instance, the hydrogenation of acetylene is an important industrial process to remove traces of acetylene in the ethylene feed for the production of polyethylene. Because acetylene poisons the catalyst for the polymerisation of ethylene to polyethylene, the acetylene content in the ethylene feed has to be reduced to the low ppm range. Moreover, economic efficiency requires high selectivity of acetylene hydrogenation in the presence of an excess of ethylene to prevent the hydrogenation of ethylene to ethane.

Typical hydrogenation catalysts contain palladium dispersed on metal oxides. While palladium metal exhibits high activity, e.g. in the hydrogenation of acetylene, it possesses only limited selectivity because of the formation of ethane by total hydrogenation and C4 and higher hydrocarbons by oligomerisation reactions.

The C3 cut (propylene) is generally purified by selective hydrogenation of propyne (methylacetylene) and propadiene (allene), and the obtained propylene may be further processed to polypropylene.

Another important selective hydrogenation in industry is the removal of traces of 1,3-butadiene from the C4 fraction after the extractive separation thereof. Pd/Al2O3 catalysts are commonly used in this reaction. Furthermore, the selective hydrogenation of 1,5-cyclooctadiene, obtained by cyclic dimerization of 1,3-butadiene, to cyclooctene on Pd/Al2O3 and of benzene to cyclohexene on ruthenium catalysts are of importance.

In all of these selective hydrogenations, further improvements of the selectivity to the desired product and an increased long term stability of the used catalyst have been strongly desired.

The use of ordered intermetallic compounds as catalysts in a variety of different reactions is generally described in US 2004/0126267 A1 and WO 2004/012290 A2. However, these documents fail to disclose the application of this type of compounds to hydrogenations, let alone selective hydrogenations. In fact, the focus of these references is on their use in fuel cells. As regards the form of the catalyst, US 2004/0126267 A1 also provides for the presence of the catalyst bed in the form of a granular powder, coated beads or a coated ceramic monolith.

The intermetallic compounds PdGa or Pd3Ga7 are described by E. Hellner et al. in Z. Naturforsch. 2a, 177-183 (1947) and by K. Khalaff et al. in J. Less-Common Met. 37, 129-140 (1974). Recently, K. Kovnir et al. in Stud. Surf. Sci. Catal., 162, 481-488 (2006) uncovered the potential of these materials as highly-selective catalysts for the acetylene partial hydrogenation. In the catalytic tests, the authors used unsupported intermetallic compounds obtained by melting the necessary amounts of palladium and gallium. Furthermore, samples obtained by milling the as-made compounds in a swing mill, and samples obtained by subjecting the as-made materials to chemical etching using aqueous ammonia solution were tested. While the activity of the as-made samples was not satisfactory, it could be enhanced by the milling and etching treatment. M. Armbrüster et al., Z. Anorg. Allg. Chem. 632, 2083 (2006) provides for a similar disclosure. However, in the case of milling, the achieved increase in activity still left room for improvements. On the other hand, the etching treatment involves a time consuming after-treatment of the as-made samples by stirring in diluted ammonia solution.

In the scientific literature, there are only few articles dealing with the mixing of catalysts with silica. For instance, A. M. Youssef et al. in Appl. Catal. A, 81, 1-13 (1992) describe the mechanical mixing of precipitated, non-washed silica hydrogel and hydrous magnesium hydroxide. The respective slurries were thoroughly mixed by mechanical stirring, filtered, washed and finally dried at 100° C., prior to thermal treatment at 500, 600 and 800° C. The obtained preparations were tested in the heterogeneous catalytic decomposition of isopropanol.

C. Wögerbauer et al., in J. Catal., 201, 113-127 (2001) describe mechanical mixtures of Ir black or IrO2 with various mixing materials like silica xerogel, alumina and H-ZSM-5. The mixtures are claimed to show outstanding DeNOx activity compared to their supported counterparts. Moreover, Pt black, Pd black and Rh black, each mixed with silica xerogel were used in the reduction of NO with propene.

The mechanical mixing and grinding of Ag nanoparticles and SiO2 powder to form a uniform mixture is described in Z. Qu et al. in Catal. Today, 93-95, 247-255 (2004). Following calcination pretreatment with oxygen at 500° C. or higher, the materials were used in CO selective oxidation. Mechanical Ag/SiO2 mixtures without calcination showed practically no activity.

In view of the above prior art, it is an object of the present invention to provide a process for the selective hydrogenation of unsaturated hydrocarbon compounds, in particular of ethyne (acetylene) in admixture with a large excess of ethene (ethylene) to afford ethene, which is further improved in terms of activity while maintaining a high selectivity, and moreover uses catalysts that can be prepared easily. It is another object to provide alternative catalysts comprising ordered intermetallic compounds having enhanced activity.

SUMMARY

The present inventors unexpectedly found that the catalytic activity of ordered intermetallic compounds, for example in hydrogenations, can be significantly increased by using them together with an inert material in a mixture such as described in the present specification. In the case of selective hydrogenations, this increase in activity is achieved while preserving the high selectivity of the catalysts, e.g. in the case of the selective acetylene hydrogenation. The present invention has been completed based on this finding.

Accordingly, the present invention pertains to a process for the selective hydrogenation of at least one unsaturated hydrocarbon compound comprising reacting the said compound with hydrogen in the presence of a hydrogenation catalyst comprising a mixture of an ordered intermetallic compound and an inert material.

According to another aspect, the present invention relates to the use of a mixture comprising at least one ordered intermetallic compound and at least one inert material, as a catalyst.

Preferred embodiments of the present invention are subject of the dependent claims.

DRAWINGS

DETAILED DESCRIPTION

Figure 1A:
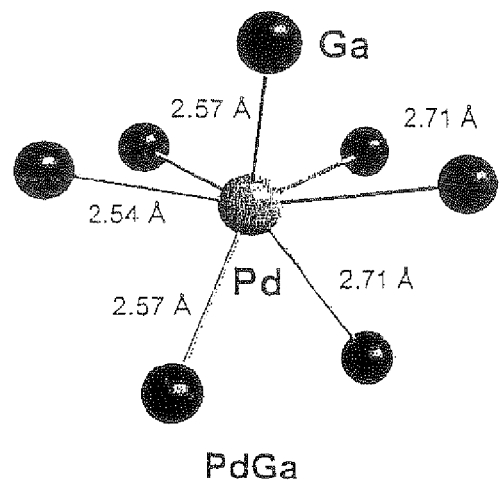
FIG. 1 shows the coordination of Pd atoms in PdGa (FIG. 1a) and in Pd3Ga7 (FIG. 1b).

The benefits of the hydrogenation process of the present invention can be achieved preferentially if the hydrogenation proceeds selectively.

Everyone active in the field of hydrogenation catalysis is familiar with the term "selective hydrogenation". Generally, a chemical reaction is referred to as being selective if it occurs with preference for one of several functional groups of similar reactivity which are present in the molecules of the reaction mixture, whereas the remaining functional groups of this type react to a significantly lower degree, i.e. they do hardly react in the case of highly selective reactions. Differently stated, a hydrogenation is selective if it selects a certain hydrogenation reaction (or certain hydrogenation reactions) from the various hydrogenation reactions which are possible in the reaction mixture. Consequently, term "selective hydrogenation" as it is used herein covers e.g., the following situations: (1) some of the unsaturations (e.g. double and/or triple bonds) of the unsaturated hydrocarbon compound to be reacted are hydrogenated with preference whereas the other unsaturations react to a significantly lower degree, and (2) in the case that one or more unsaturations of the unsaturated hydrocarbon compound to be reacted can be hydrogenated twice (e.g. triple bonds), they are hydrogenated with preference only once, and the 2nd reaction step is hardly observed. For the purpose of the present invention, a hydrogenation is referred to as selective if the molar ratio of the desired target compound to the undesired target compound(s) is larger than 1:1, preferably more than 2:1, more preferably more than 5:1, and most preferably 10:1.

A typical example of situation (1) is the hydrogenation of an alkadiene to afford mainly, preferably almost exclusively, the corresponding alkene without substantial reaction of the alkene to the corresponding alkane. Situation (2) may be exemplified by the reaction of an alkyne to give mainly the corresponding alkene, whereas the consecutive reaction of the alkene to afford the alkane hardly takes place. As will be appreciated from the above, the two situations are not mutually exclusive. That means, both of the above situations may exist in the selective hydrogenation of a specific molecule. In the case of the acetylene reaction in a large excess of ethylene which corresponds to situation (2), it is important that the ethylene, in spite of its large concentration, is hardly converted to ethane.

Examples of selective hydrogenations are described in the Background Art section of the present specification.

The unsaturated hydrocarbon compound used in the selective hydrogenation process of the present invention is not limited in kind as long as this contains one or more unsaturations susceptible to hydrogenation and poses a selectivity problem as outlined above. For example, the unsaturated hydrocarbon compound may be an unsaturated carbonyl compound, e.g. a compound having both a carbonyl moiety and a carbon-carbon double bond in the molecule. However, the unsaturated hydrocarbon compound preferably contains, as unsaturations susceptible to hydrogenation, carbon-carbon double and/or carbon-carbon triple bonds, and is free from further unsaturations susceptible to hydrogenation, i.e. hydrogenable group(s). According to a more preferred embodiment, the unsaturated hydrocarbon compound is selected from the group consisting of alkadienes, alkatrienes and alkapolyenes; alkynes, dialkynes, trialkynes and polyalkynes; and aromatic compounds. The alkadienes, alkatrienes and alkapolyenes, and the alkynes, dialkynes, trialkynes and polyalkynes cover both, alicyclic and cyclic compounds. Still more preferably, the unsaturated hydrocarbon compound is selected from the group of alkadienes, cycloalkadienes, alkynes and benzene.

The alkadiene may be 1,3-butadiene, which will be converted by way of the selective hydrogenation of the present invention, mainly to 1-butene, without being fully hydrogenated to butane to a significant degree. The cycloalkadiene is, for example, 1,5-cyclooctadiene which will afford upon the selective hydrogenation of the invention cyclooctene, while cyclooctane resulting from the full hydrogenation is a minor product. The selective hydrogenation of benzene will afford cyclohexene with minor amounts of cyclohexadiene and cyclohexane. An example of a selective hydrogenation of a triple bond in the presence of a double bond is the purification of 1,3-butadiene by hydrogenation of vinyl acetylene present in the mixture. Still another example of a selective hydrogenation is the reaction of nitrobenzene to aniline.

The alkyne is preferable ethyne (acetylene), and this is the most preferred embodiment of the present invention. Through the process for the selective hydrogenation of the invention, ethyne will predominantly be converted to ethene (ethylene) while the hydrogenation of ethene to afford ethane is negligible. This is even so when the selective hydrogenation of ethyne is carried out under reaction conditions where ethyne is present in admixture with an excess of ethene in relation to ethyne, which is a particularly preferred embodiment of the selective ethyne hydrogenation according to the present invention. Most preferably, ethene is present in the reaction mixture to be hydrogenated in a large excess in relation to ethyne. The ethyne to ethene weight ratio in the starting mixture of the selective ethyne hydrogenation of the invention is preferably 1:10 to 1:10⁶, more preferably 1:50 to 1:10³. In industrial processes, the ethene to ethyne weight ratio in the mixture obtained after the selective hydrogenation is typically as large as >10⁶.

The selective hydrogenation of phenyl acetylene to styrene in excess of styrene is another example of a selective hydrogenation. As will be appreciated, that reaction is the polystyrene counterpart of the selective acetylene hydrogenation in excess of ethylene in the feed used for the preparation of polyethylene.

As used herein, the term "ordered intermetallic compound" refers to a compound that consists of more than one metal and has an ordered crystal structure. For the purpose of the present specification, boron (B), silicon (Si), phosphorus (P) and arsenic (As) are regarded as "metals" since they can form intermetallic compounds. In the ordered crystal structure, substantially all unit cells include the same arrangement of metal atoms.

It will be appreciated that defects which usually cannot be completely avoided in a real crystal may be present in the ordered intermetallic compound contained in the mixture for us as a catalyst. Such defects can cause a small number of unit cells in the ordered intermetallic compound to have an arrangement of metal atoms different from the majority of the unit cells. Defect types include for example vacancies, interstitials, atom substitutions and anti-site defects.

Crystal imperfections due to the presence of defects will lead to a certain homogeneity range of the ordered intermetallic compound. However, the formulae used in the present specification refer to the ideal crystal structure. As will be appreciated from the above, the stoichiometric ratio of the metals forming the ordered intermetallic compound as used in the formula may vary up and down. To give an example, if a binary ordered intermetallic compound is represented by the general formula AxBy, then x and y may independently be an integer of 1 or more. In the present specification, AB (i.e. x=y=1) and A3B7 represent ordered intermetallic compounds having a certain stoichiometric ratio of the constituent metals (for example, PdGa and Pd3Ga7). Taking account of the above homogeneity range the values of x and y may be slightly greater or slightly less than the integers indicated in the formula. The range of the numerical values for the respective ordered intermetallic compound can be taken from the phase diagram the compound. It corresponds to the respective single-phase region of the constituent metals. For instance, it can be taken from the phase diagram of Pd3Ga7 at 300° C. that the actual value of x in PdxGay is between 2.99 and 3.06.

The ordered intermetallic compounds for use in the present invention may have a variety of stoichiometric ratios. Preferably, the ordered intermetallic compounds are binary compounds, i.e. those comprising two types of metals, but they may also be ternary or multinary intermetallic compounds. An example of a ternary ordered intermetallic compound for use in the present invention is Pd2PtGa3.

The ordered intermetallic compounds as meant in the present invention are to be distinguished from metal alloys and metal solid solutions. Alloys and solid solutions do not have an ordered atomic structure, as described above. Rather, metal atoms are arranged randomly in unit cells of alloys and solid solutions.

Ordered intermetallic compounds also generally have a more stable atomic arrangement in comparison to alloys and solid solutions. This results in an enhanced lifetime of the catalyst under reaction conditions. In alloys and solid solutions, atoms are prone to migration with an associated reduction of catalytic performance.

The ordered intermetallic compound for use in the present invention preferably comprises at least one metal of type A capable of activating hydrogen, and at least one metal of type B not capable of activating hydrogen, and the structure of the ordered intermetallic compound is such that at least one kind of type A metals, preferably all type A metals, is mainly surrounded by atoms of the metal of type B. In this context, the term "mainly" accounts for the fact that there may be defects due to atom substitutions so that there may be some metals of type A in the crystal structure of the intermetallic compound, in the first coordination sphere of which there are also one or more of type A metal atoms. The above requirement of being mainly surrounded is intended to mean that more than 50%, preferably at least 80%, more preferably at least 90%, and most preferably about 100% of the first coordination sphere of least one kind of the type A metals is occupied by atoms of type B metals.

Figure 1B:
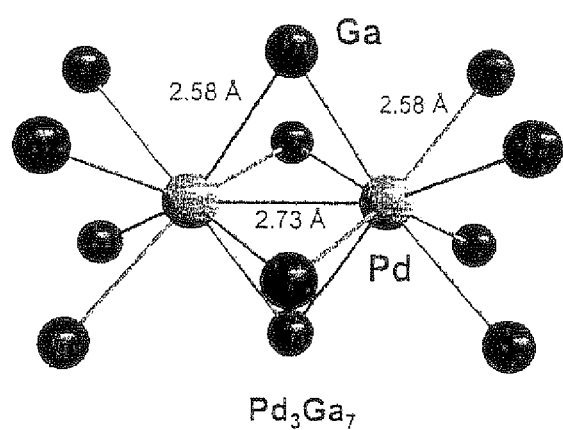

The above situation of the type A metal atoms (Pd) being mainly, more specifically exclusively surrounded by type B metal atoms (Ga) is illustrated for PdGa in FIG. 1a, and for Pd3Ga7 in FIG. 1b. The preferred embodiment of the ordered intermetallic compound for use in the present invention where the type A metal atoms are completely surrounded by type B metal atoms, i.e. where about 100% of the first coordination sphere of the at least one kind of type A metal is occupied by atoms of type B metals does, however, not exclude the presence of defects. The feature that the structure of the ordered intermetallic compound is such that at least one kind of type A metals, preferably all type A metals, is surrounded mainly by atoms of the metal of type B indicates that the atoms of type A metal are predominantly coordinated to atoms of type B metals, i.e. coordinated >50%, preferably at least 80%, and more preferably about 100% to type B metals.

The molar ratio of the metals of type A and B (A:B) in the ordered intermetallic compound for use in the present invention may be from 20:1 to 1:20. Typically it is from 2:1 to 1:20, preferably from 1:1 to 1:20, more preferably from 1:1 to 1:5. The metal of type A is not limited in kind, as long as it is capable of activating hydrogen. However, Ti, Zr, Hf, V, Nb, Ta, Cr, Mo, W, Mn, Re, Fe, Ru, Os, Co, Rh, Ir, Ni, Pd, Pt, Cu, Ag, and Au are preferred. Cr, Mo, W, Fe, Co, Rh, Ni, Pd and Pt are more preferred. There is no particular limitation of the metals of type B, either. According to a preferred embodiment, these metals are selected from the group consisting of B, Al, Ga, In, Tl, Si, Ge, Sn, Pb, P, As, Sb, Bi, Zn, Cd and Hg, i.e. the metals of the groups 12, 13, 14 and 15 of the Periodic Chart. According to a preferred embodiment, the mentioned metals e.g. of the groups 12, 13, 14 and 15 of the Periodic Chart as type B metals are combined with palladium and/or platinum and/or another type A metal to form the ordered intermetallic compound, which is more preferably a binary ordered intermetallic compound.

The intermetallic compound for use in the present invention is more preferably selected from intermetallic compounds of Pd with at least one of B, Al, Ga, In, Tl, Si, Ge, Sn and Zn, intermetallic compounds of Pt with at least one of Al, Ga, In, Tl, Sn and Zn, and intermetallic Pd/Pt compounds with at least one of Al, Ga, In, Tl and Sn, such as Pd2PtGa3. Preferably, the ordered intermetallic compound is a binary compound of Pd in combination with B, Al, Si, Ge, Zn or Ga, more preferably it is a binary compound of Pd in combination with Ge, Zn or Ga.

According to another preferred embodiment, the ordered intermetallic compound for use in the present invention is an ordered binary Pd—Ga intermetallic compound. Due to electronic factors associated with the ratio of electronegativities, binary Pd—Ga intermetallic compounds excel in structural stability. According to still another preferred embodiment, the ordered intermetallic compound is a binary compound of Pt in combination with Zn. The above intermetallic compounds, in particular ordered binary intermetallic compounds comprising Pd are preferably used in the selective hydrogenation of carbon-carbon multiple bonds, especially the selective hydrogenation of carbon-carbon triple bonds to give the corresponding alkene. Thereby, the structure of the intermetallic compounds may be such that more than 50% of the first coordination sphere of at least one kind of type A metals is occupied by metals of type B, as defined above. The compounds to be hydrogenated are preferably free of any unsaturated groups amenable to hydrogenation other than the carbon-carbon triple bond(s).

The specific ordered intermetallic compound for use in the present invention can be selected from the group consisting of Pd2Ga, PdGa, PdGaS, Pd3Ga7, PdSn, PdSn2, Pd2Ge, Pd2Si, PdSi, PdGe, PdZn, PtGa and PtZn. Preferably it is PdGa, Pd2Ga, PdGaS or Pd3Ga7, and more preferably it is PdGa, Pd2Ga or Pd3Ga7. PdGa and Pd3Ga7 in particular proved to have an excellent structural stability under various reaction conditions, e.g. in reactive gas atmospheres of hydrogen, various hydrocarbons, carbon monoxide and oxygen, in particular under reaction conditions which are typically employed in industrial selective hydrogenations, e.g. temperatures from room temperature to about 227° C. Consequently, the individual ordered intermetallic compounds listed above may be used in the selective hydrogenation of any unsaturated hydrocarbon, in particular, in the following reactions: (cyclo)alkadiene→(cyclo)alkene and alkyne→alkene (in particular, ethyne→ethene).

In a particular preferred embodiment of the selective hydrogenation process of the invention, the at least one unsaturated hydrocarbon compound is ethyne (acetylene), and the at least one intermetallic compound for use in the present invention is an ordered binary Pd—Ga intermetallic compound, preferably PdGa or Pd3Ga7. Even more preferably, the selective hydrogenation of ethyne to ethene is carried out with the above ordered intermetallic compounds under reaction conditions where the ethyne starting material is present in admixture with ethene, the ethene being present in large excess in relation to ethyne.

The ordered intermetallic compounds for use in the present invention offer distinct advantages in selective hydrogenations, over supported monometallic catalysts of the prior art, such as supported palladium, platinum and rhodium catalysts, and over alloyed or promoted palladium catalysts, in terms of selectivity to the desired product. Without wishing to be bound by theory, it is assumed that the enhanced selectivity is due to the defined structure of active sites in the ordered intermetallic compounds allowing only certain adsorption geometries of the unsaturated hydrocarbon compound to be hydrogenated. For instance, where the structure of the ordered intermetallic compound is such that at least one metal of type A, preferably all type A atoms in the structure of the ordered intermetallic compound are mainly surrounded by type B atoms, the individual atoms of the type A metals are isolated. This is considered to avoid an oversupply of activated hydrogen, and leads to an enhanced selectivity. Moreover, due to the isolation of type A atoms, only certain adsorption geometries of the reactants are possible.

As used herein, the inert material is intended to mean any material that is substantially, preferably completely devoid of any catalytic activity in the reaction, e.g. the selective hydrogenation to be catalyzed. Consequently, the inert material, when subjected to a blank catalytic measurement does not show any (substantial) catalytical activity in the reaction at issue. Examples of the inert material for use in the present invention are silica, silica gel, kieselguhr and silicates. Moreover, alumina, titania, zirconia, zeolites, active carbon, talc, kaolin, boron nitride and clays can be exemplified.

Preferably, the inert material has a high specific surface area that is typically in the range of 10 to 2000 m2/g, e.g. 100 to 1500 m2/g, and especially 300 to 1200 m2/g.

According to a preferred embodiment, the inert material is silica, in particular silica having a specific surface area of 100 to 500 m2/g. Suitable types of silica having a high surface area are commercially available. Examples are γ-SiO2 (Degussa AG) and various types of Aerosil®. Types of Aerosil® exemplarily used as a silica inert material in the present invention are Aerosil® 300 and Aerosil® 300 SP, both manufactured by Degussa Evonik. For the purpose of the present specification, the specific surface area of the materials refers to the specific surface area as measured according to the BET method using nitrogen as an adsorbent.

According to another preferred embodiment, the inert material is alumina. While the alumina is not specifically limited in kind, it is preferably a type of alumina having a specific surface area of 100 to 500 m2/g. As regards the pH, neutral, acidic or basic alumina may be used, with neutral alumina being preferred. A commercially available neutral alumina exemplarily used as an inert material in the present invention is the activated neutral alumina Brockmann I, Sigma Aldrich 199974.

The mixture for use in the present invention is to be distinguished from a supported catalyst comprised of the ordered intermetallic compound and the inert material, as a support. In the case of a supported catalyst, the catalytically active component is applied to the support, e.g. by impregnation, such as incipient wetness impregnation, with subsequent drying, calcination and reduction in situ in a hydrogen stream at elevated temperatures. Another method of preparing a supported catalyst is by way of precipitation. As a consequence of their preparation, the catalytically active compound will be fixed onto and adhere to the inert material support in the case of a supported catalyst. This is different for the mixture of the present invention where the components constituting the mixture, i.e. the at least one ordered intermetallic compound and the at least one inert material are unfixed and can flow freely. Consequently, the mixture for use in the present invention can be separated, e.g. by flotation, into the inert material(s) and the ordered intermetallic compound(s), whereas this is not possible in the case of a corresponding supported catalyst.

The mixture for use in the present invention is preferably a mixture of the ordered intermetallic compound and the inert material, as homogeneous as possible. That means partial volumes of the mixture as small as possible contain the ordered intermetallic compound(s) and the inert material(s) in substantially the same proportions.

According to a preferred embodiment, the mixture for use in the present invention is a dry mixture. For the purpose of the present invention, a mixture is referred to as "dry" when no water or other solvents are added upon preparing the mixture, for example from the ordered intermetallic compound obtained by melting together the constituent metals (with an optional subsequent comminution step), and the inert material obtained from the supplier. This embodiment of the mixture is particularly useful in the case of selective hydrogenations which are carried out in the gas phase.

The presence of one type and of more than one type of each of the ordered intermetallic compound and the inert material in the mixture is encompassed by the present invention. However, for the ease of manufacturing, the mixture preferably comprises just one type of each of these components.

The ratio of the ordered intermetallic compound(s) and the inert material(s) in the mixture for use in the present invention is not particularly limited. However, for cost reasons, the inert material is preferably present in the mixture in an excessive amount. For instance, the ratio of the at least one ordered intermetallic compound and the at least one inert material is from 1:5 to 1:1000 by weight, preferably it is between 1:5 to 1:500 by weight, and most preferably it is from 1:10 to 1:300 by weight.

The mixture can generally be prepared by stirring the components constituting the same. General mixers can be used for preparing the mixture. In the case of dry mixtures, for instance, the ordered intermetallic compound and the inert material can be ground, e.g. using a mortar. On an industrial scale, rotary mixers such as rotary-drum mixers, mixers with moving mixing tools and pneumatic mixers can be used. Also, large amounts of the mixture can be prepared by using ball mills, such as planetary mills or swing mills. When preparing the mixture by using planetary mills, which is a preferred embodiment of the present invention, the conditions may be for instance 200 to 400 rpm for silica (such as Aerosil® 300 or Aerosil® 300 SP) and in the range of 200 to 300 rpm for alumina, in particular neutral alumina (such as Brockmann I, Sigma Aldrich 199974), in view of the selectivity and stability of the mixture as a catalyst in selective hydrogenations. Dependent on the kind of inert material, in some cases, the mixture prepared by using planetary mills, in comparison to a corresponding mixture obtained by grinding in a mortar exhibited an enhanced selectivity e.g. to ethylene in the selective hydrogenation of acetylene in the presence of an excess of ethylene.

According to specifically preferred embodiments, the ordered intermetallic compound is a binary Pd—Ga intermetallic compound, in particular PdGa which is used together with silica or alumina in the mixture. Moreover, the said mixture, preferably in dry form, is preferably used for the selective hydrogenation of acetylene to afford ethylene even when there is a large excess of ethylene in the reaction mixture.

Figure 3A:
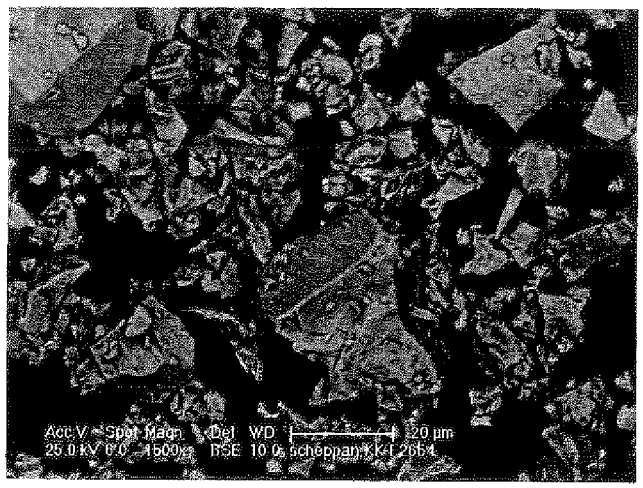
FIG. 3 shows SEM images (magnification 1500×) of mortar-grinded PdGa (FIG. 3a) and PdGa after mixing with silica (FIG. 3b).
Figure 3B:

FIG. 3 shows microscopic images of mortar-grinded PdGa (FIG. 3a) and PdGa after mixing with silica (FIG. 3b). The SEM (scanning electron microscope) investigations show that mixing with silica in accordance with the present invention results in diminishing the largest PdGa particles and decreasing the average particle size, in comparison to mortar-grinded PdGa.

The ordered intermetallic compounds for use in the present invention can for instance be manufactured by melting an amount of the constituent metals suitable to form the intermetallic compound. The metals used for forming the melt are present in a molar ratio corresponding to their molar ratio in the intermetallic compound. Preferably, the melting of the metals is carried out under inert gas atmosphere, such as argon and nitrogen, preferably argon. This manufacturing method is standard in solid state chemistry. The method of preparing PdGa and Pd3Ga7 is, for example, described in the working examples of the present application, and in more detail in R. Giedigkeit, Diploma thesis, Technische Universität Darmstadt (Germany), 1998, the contents of which is herewith incorporated by reference in its entirety. In addition, reference can be made to the paper by K. Kovnir et al. cited in the background art section of the present specification.

The preparation of some ordered intermetallic compounds may involve annealing steps, e.g., where the respective compound does not crystallize from the melt. To give an example, this is necessary for Pd3Ga7 which does not show congruent melting behavior. Looking at the phase diagram of the respective intermetallic system, the skilled person will conclude where annealing is necessary to achieve the thermodynamic equilibrium of the sample so that the thermodynamically most stable modification is formed. The annealing is preferably carried out for an amount of time and temperature as large as possible.

In the above methods, the ordered intermetallic compound is usually obtained in the form of a solidified molten mass. The mass can be directly formed into the mixture for use in the present invention by grinding the mass together with the inert material.

Preferably, the molten mass is comminuted, e.g. by grinding, prior to mixing with the inert material.

In the alternative, the comminuted mass of the ordered intermetallic compound, e.g. the binary Pd—Ga intermetallic compound can be subjected to further treatments prior to preparing the mixture with the inert material. For instance, the further treatment may be, e.g. in the case of Pd—Ga binary intermetallic compounds, an etching treatment as described below and also in K. Kovnir et al. in Stud. Surf. Sci. Catal. 162, 481-488 (2006).

The etching may be achieved by chemical etching, e.g. by using alkaline etching solutions and complexing amines, such as EDTA and derivatives, dependent on the particular ordered intermetallic compound to be etched. Useful alkaline etching solutions are, for example, aqueous alkali hydroxide (e.g. sodium and potassium hydroxide) and alkaline earth hydroxide solutions, and aqueous ammonia solutions. In the case of ordered intermetallic palladium gallium compounds, in particular of PdGa and Pd3Ga7, the use of an alkaline etching solution having a pH in the range of 8.0 to 10.5 yielded hydrogenation catalysts showing in the selective hydrogenation of acetylene a higher activity while maintaining an excellent selectivity and catalyst lifetime. In the case of PdGa a pH of about 9.0 and in the case of Pd3Ga7 a pH of 10.5 gave the best results in terms of activity in the selective hydrogenation of acetylene.

While the catalytic activity of the ordered intermetallic compounds can be increased by way of the surface etching, the selectivity, e.g. in the acetylene reaction, may be slightly reduced upon etching. To regain the selectivity of the unetched ordered intermetallic compound, a tempering at reduced temperature to effect a sintering of the palladium particles can be carried out. Suitable temperatures for the tempering are 50-500° C., preferably 80-400° C., most preferably 100-300° C.

The above etching (possibly followed by a tempering treatment at reduced temperature) of the ordered intermetallic compound can be expected to increase the activity of the resultant mixture even further. On the other hand, the additional etching contributes to the complexity of the method of preparing the mixture for use in the present invention. For this reason, the ordered intermetallic compound, e.g. prepared by melting the constituent metals (with optional subsequent annealing and comminuting steps) is preferably directly formed into the mixture by mixing with the inert material without additional treatment steps such as etching.

The hydrogenation catalyst for use in the process of the invention may contain components in addition to the mixture of the at least one ordered intermetallic compound and the at least one inert material. Such components may be metals being catalytically active in the hydrogenation at issue. However, the mixture preferably constitutes at least 95%, more preferably at least 99% of the hydrogenation catalyst. Most preferably, the hydrogenation catalyst does not contain any components other than the mixture, i.e. it consists of the mixture.

Catalyst screening methods may be used to readily determine which ordered intermetallic compounds in the mixture for use in the present invention are well-suited to catalyse a particular reaction, such as (selective) hydrogenation. Suitable screening methods are described in A. Hagemeyer, A. Strasser, P. Volpe, F. Anthony, High-throughput screening in heterogeneous catalysis: Technologies, strategies and applications, Wiley-VCh, Weinheim, 2004.

Moreover, a skilled person in the field of catalysis will readily select and optimise the reaction conditions for the reaction, e.g. selective hydrogenation at issue. For instance, the temperature range of industrial selective hydrogenations is typically 10° to 300° C., preferably 20° to 250° C., most preferably 30° to 200° C. The pressure is generally 1 to 100 bar, preferably 2 to 75 bar, most preferably 5 to 50 bar. For more details, reference is made to WO 03/106020.

According to another aspect, the present invention is concerned with the use of a mixture of the at least ordered intermetallic compound and the at least one inert material, as a catalyst. Preferred embodiments of the ordered intermetallic compound(s) and inert material(s) in the mixture are the same as those described herein in connection with the selective hydrogenation process.

The following Examples are given for illustration of the invention and must not be construed as limiting the present invention.

EXAMPLES

Synthesis of PdGa 1.2083 g palladium (ChemPur 99.95%) and 0.7917 g gallium (ChemPur 99.99%) were molten in glassy carbon crucibles under argon atmosphere in a high-frequency induction furnace to obtain 2 g PdGa (11.354 mmol). After cooling, the solidified molten mass was taken out and subjected to grinding in a mortar. This material is referred to as as-made PdGa, below.

The crystal structure of the product was controlled by X-ray diffractometry using a STOE STADI P diffractometer (Cu K$\alpha$1 radiation, curved Ge monochromator) in transmission geometry with a linear position sensitive detector and comparison with reference data from the literature.

Preparation of Catalysts

Example 1

The as-made PdGa was ground together with silica ($\gamma$-SiO2, Degussa AG, specific surface area: about 300 m2/g) in a mass ratio of PdGa:SiO2 of 1:10 using a mortar.

Example 2

The as-made PdGa was ground together with neutral Al2O3 (activated, neutral aluminium oxide, specific surface area of 155 m2/g, Sigma-Aldrich) in a mass ratio of PdGa:Al2O3 of 1:200 using a mortar.

Comparative Example 1

The as-made PdGa was used without further treatment.

Comparative Example 2

The as-made PdGa was powdered in a swing mill (Retsch MM 200, 4 ml WC pot, 2 WC balls) in air for 2×30 min at 25 Hz.

Comparative Example 3

Commercial ammonia solution (Merck, 25% p.a.) was diluted with water to a pH value of 9.0. PH-measurements were performed with a Knick pH-Meter 761 Calimatic and a Mettler-Toledo Inlab 422 electrode calibrated with buffer solutions (Merck centiPUR pH=7 and pH=9). 50 mg as-made PdGa was added to 75 ml of the diluted ammonia solution and stirred for 10 minutes at 300 K. The solution was filtrated under Argon flow and washed with additional 50 ml of the diluted ammonia solution. The etched sample was dried by evacuation for 120 min in a desiccator and stored under Ar in a glove box.

Comparative Example 4

Comparative Example 3 was repeated except that the pH value of the aqueous ammonia solution was adjusted to 9.8 by adding water.

Catalytic Measurements

Catalytic investigations were performed in a plug flow reactor consisting of a quartz tube with a length of 300 mm, an inside diameter of 7 mm and equipped with a sintered glass frit to support the catalyst bed. For temperature control, a thermocouple was located next to the heating wire wound around the reactor. A second thermocouple was placed inside the reactor to measure the temperature of the catalyst bed. The reactant gases were mixed with Bronkhorst mass flow controllers (total flow 30 ml/min). A Varian CP 4900 Micro gas chromatograph (GC) was used for effluent gas analysis. The Varian MicroGC contains three modules, each with an individual column and a thermal conductivity detector. Hydrogen and helium of the feed gas, and possible oxygen and nitrogen impurities because of leaks in the set-up were separated on a molsieve column. Acetylene, ethylene, and ethane were separated on an alumina column. The total concentration of C4 hydrocarbons (1-butyne, 1-butene, 1,3-butadiene, n-butane, trans and cis-2-butene) was determined using a siloxane (dimethylpolysiloxane) column. Higher hydrocarbons were also separated on the siloxan column but not further quantified because of the presence of many different C6 and C8 hydrocarbons and their low total concentration (less than 0.1% of absolute product stream concentration). Argon (6.0) and helium (6.0) were used as carrier gases for the molsieve column and for the other columns, respectively. A measurement cycle including stabilization, sampling, injection, and separation took between 4 and 5 minutes.

Acetylene hydrogenation experiments were carried out under the condition of 0.5% acetylene, 5% hydrogen, and 50% ethylene in helium. All gases were obtained from Westfalen Gas (Germany).

Activity and selectivity of the materials in the hydrogenation of acetylene were measured by temperature-programmed and by isothermal experiments. The experiments were performed at 473 K in the isothermal mode. The conversion rate was calculated using the following equation:

$$Conv = \frac{(C_{bypass} - C_x)}{C_{bypass}}$$

where Cx is the acetylene concentration in the product stream and Cbypass is the acetylene concentration in the feed before the reaction. The selectivity was calculated from the following equation, with Cbypass being the acetylene concentration before the reactor and Cx the acetylene concentration after the reactor:

$$Sel = \frac{(C_{bypass} - C_x)}{C_{bypass} - C_x + C_{ethane} + 2xC_{C4Hx}}$$

Calculation of the selectivity assumes that acetylene is only hydrogenated to ethylene, which may be further hydrogenated to ethane. The amount of C6 and higher hydrocarbons, and of carbon deposits formed was supposed to be negligible. In addition to hydrogenation of acetylene to ethane, ethylene from feed may be hydrogenated to ethane, which is included in the selectivity equation. In order to measure selectivity in acetylene hydrogenation at the same conversion, different amounts of catalysts were used according to their specific activity determined in a previous experiment.

Activity of the samples was calculated using the following equation:

$$Act = \frac{ConvC_{feed}C_{exp}}{m_{cat}}$$

where Conv is the calculated acetylene conversion, Cfeed is the concentration of acetylene in feed, i.e. 0.5%, mcat the amount of used catalyst in g and constant Cexp is 1.904 g/h and contains experimental parameters like total gas flow (30 ml), temperature (300 K) and pressure (1013 mbar) and is based on the perfect gas model.

Except for Example 1, the samples were diluted with 50 mg boron nitride (hexagonal, 99.5%, 325 mesh, Aldrich) prior to conducting the catalytic tests. In the case of the examples in accordance with the invention, blank measurements with only γ-SiO2 (Example 1) and only alumina (Example 2) in the reactor revealed absence of any catalytical activity in the hydrogenation reaction.

Results of Catalytic Testing

The results of the catalytic testing in the selective hydrogenation of acetylene as described above are summarized in Table 1, below.

TABLE 1

| Example | Sample treatment | Mass of PdGa [mg] | Acetylene conversion [%] | Selectivity [%] | Activity [gC$_2$H$_2$/gcat · h] |
|---|---|---|---|---|---|
| Ex. 1 | Mixed with silica | 8 | 93 | 68 | 1.11 |
| Ex. 2 | Mixed with Al2O3 | 0.3 | 60 | 75 | 25.00 |
| Comp. Ex. 1 | None | 400 | 64 | 77 | 0.02 |
| Comp. Ex. 2 | Milled in air | 20 | 91 | 70 | 0.43 |
| Comp. Ex. 3 | Etched at pH = 9.0 | 5 | 93 | 64 | 1.77 |
| Comp. Ex. 4 | Etched at pH = 9.8 | 1.5 | 91 | 56 | 5.78 |

Figure 2A:
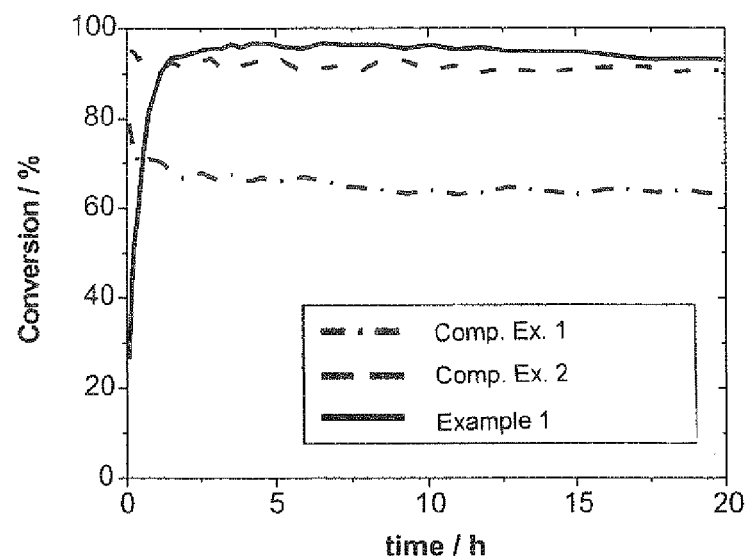
FIG. 2 shows the conversion (FIG. 2a) and selectivity (FIG. 2b) of as-prepared PdGa (400 mg), PdGa milled in air (20 mg) and PdGa mixed with silica (89 mg of mixture, 8 mg of PdGa) in the hydrogenation of acetylene in admixture with an excess of ethylene at 200° C.
Figure 2B:
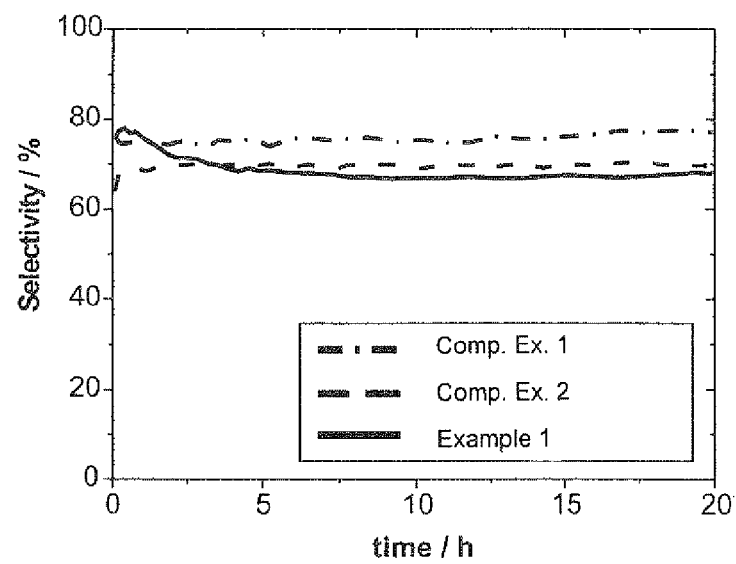

The acetylene conversion and the corresponding selectivity to ethene obtained for the catalysts of Example 1, and Comparative Examples 1 and 2 are shown in FIG. 2a and FIG. 2b. As can be seen from the figures, the mixture for use as a catalyst in the present invention achieves a superior conversion while preserving a high selectivity.

By using alumina instead of silica as the inert material in the mixture, the activity can be enhanced even further. This is evident from the results reported in Table 1 for Example 2. As shown in the righthand column of the table, the activity is increased in the case of alumina as an inert material by a factor of nearly 60 compared to milled PdGa (cf. Comparative Example 2).

Preparation of Further Catalysts

Materials used:

PdGa was prepared as described in the above Section "Synthesis of PdGa". As inert materials, there were used silica and alumina. The silica used was Aerosil® 300 SP (Degussa Evonik). As alumina, activated neutral Brockmann I, Sigma Aldrich 199974 was used.

Procedures for Preparing Mixtures:

The components of the mixture were ground in a mortar in air until a homogeneous mixture is obtained. This is referred to as sample preparation "H", hereinafter.

Another sample treatment involves subjecting the components of the mixture to milling in a planetary mill (Syalon milling tool) at 200 rpm in air for 5 minutes. This is denoted sample preparation "S1", below.

According to still another treatment procedure, the components of the mixture were subjected to milling in a planetary mill (tungsten carbide milling tool) in air under the following conditions: 200 rpm for 5 minutes; subsequently four times 200 rpm for 5 minutes each with an interruption of 5 minutes in-between, and then four times 400 rpm for 5 minutes each with an interruption of 5 minutes in-between. This procedure is referred to as sample preparation "W1" hereinafter.

Using the above materials and sample preparation procedures, several mixtures as identified in Table 2, below were prepared.

TABLE 2

| Example | Total amount of mixture prepared [g] | Composition of mixture (by weight) | Inert material | Sample preparation |
|---|---|---|---|---|
| Ex. 3 | 5 | 5% PdGa + 95% Al2O3 | alumina[1] | H |
| Ex. 4 | 10 | 5% PdGa + 95% Al2O3 | alumina[1] | S1 |
| Ex. 5 | 0.08 | 10% PdGa + 90% SiO2 | silica[2] | H |
| Ex. 6 | 0.8 | 10% PdGa + 90% SiO2 | silica[2] | W1 |

[1] Activated neutral Al2O3, Brockmann I, Sigma Aldrich 199974
[2] Aerosil 300 SP Catalytic Testing The above mixtures were used as catalysts in the selective hydrogenation of acetylene to ethylene in excessive ethylene as detailed in the above Section "Catalytic measurements", except that the sample mixtures were each diluted with 150 mg boron nitride. The results of the catalytic tests are summarized in Table 3, below. In the catalytic tests the catalyst mixtures were used in amounts corresponding to the calculated mass of PdGa that is shown in the second column of the table.

TABLE 3

| Example | Mass of PdGa [mg] | Acetylene conversion [%] | Selectivity [%] | Activity [gC$_2$H$_2$/gcat · h] |
| --- | --- | --- | --- | --- |
| Ex. 3 | 3.0 | 60 | 80 | 2.09 |
| Ex. 4 | 1.0 | 56 | 78 | 5.86 |
| Ex. 5 | 8.0 | 95 | 64 | 1.24 |
| Ex. 6 | 1.2 | 96 | 57 | 8.37 |

Figure 4:
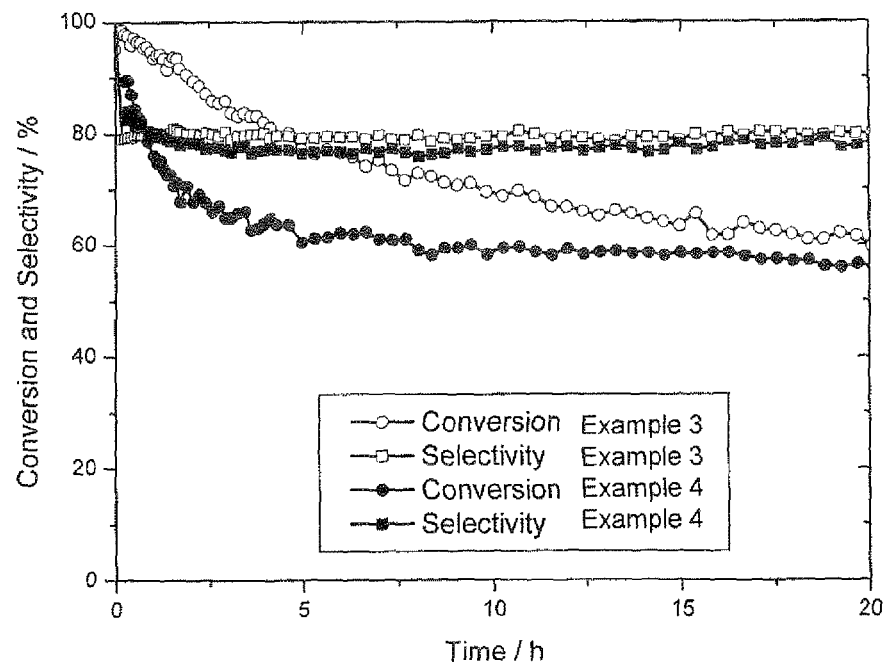
FIG. 4 shows the conversion and selectivity of the hydrogenation catalysts prepared in Examples 3 and 4 (mixtures of PdGa and alumina) in the hydrogenation of acetylene in admixture with an excess of ethylene at 200° C.
Figure 5:
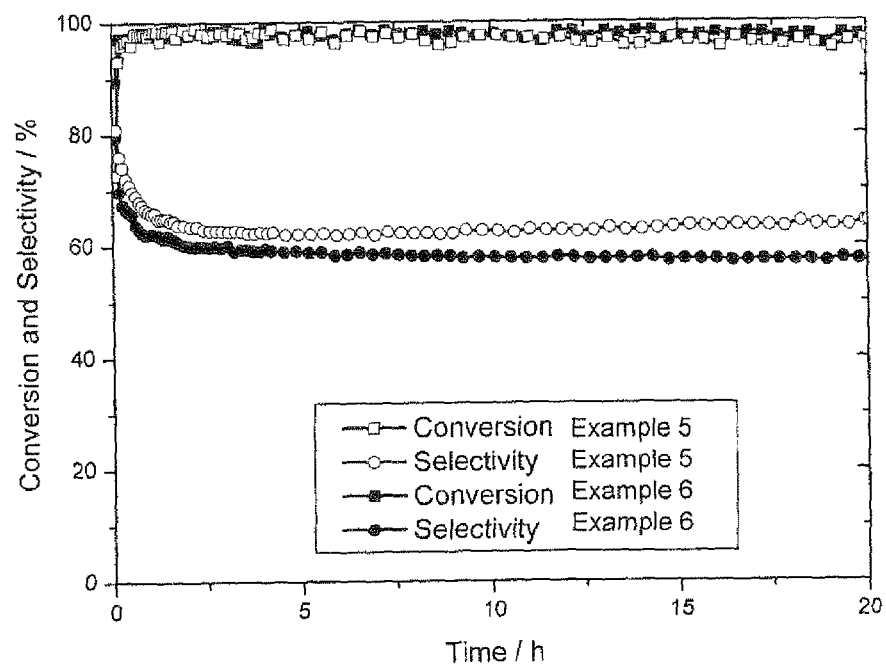
FIG. 5 shows the conversion and selectivity of the hydrogenation catalysts prepared in Examples 5 and 6 (mixtures of PdGa and Aerosil® 300 SP) in the hydrogenation of acetylene in admixture with an excess of ethylene at 200° C.

The conversion and selectivity of the catalyst mixtures of Examples 3 and 4 (using activated neutral alumina as an inert material) is shown in FIG. 4, and the conversion and selectivity of the catalyst mixtures of Examples 5 and 6 (using Aerosil® 300 SP as an inert material) is shown in FIG. 5.

As can be seen from the above experimental results, the hydrogenation catalysts comprising a mixture of an ordered intermetallic compound (such as PdGa) and an inert material (such as silica or alumina) can be prepared in large amounts using automated milling e.g. in planetary mills, thus enabling industrial use, while obtaining highly active and selective catalysts, e.g. in the selective hydrogenation of acetylene in the presence of excessive ethylene.

What is claimed is:

1. A process for the hydrogenation of at least one unsaturated hydrocarbon compound comprising reacting the at least one unsaturated hydrocarbon compound with hydrogen in the presence of a hydrogenation catalyst, wherein the hydrogenation catalyst comprises a mixture of an ordered intermetallic compound and an inert material, wherein the ordered intermetallic compound is a binary Pd—Ga intermetallic compound.

2. The process according to claim 1, wherein the ordered intermetallic compound is selected from the group consisting of Pd$_2$Ga, PdGa, PdGa$_5$ and Pd$_3$Ga$_7$.

3. The process according to claim 1, wherein the structure of the ordered intermetallic compound is such that more than 50% of the first coordination sphere of the Pd atoms is occupied by Ga atoms.

4. The process according to claim 1, wherein the inert material is selected from the group consisting of silica, alumina, titania, zirconia, zeolites, active carbon, talc, kaolin, boron nitride and clays.

5. The process according to claim 4, wherein the inert material is silica or alumina, each having a BET specific surface area of 100 to 500 m$^2$/g.

6. The process according to claim 1, wherein the mixture is a dry mixture.

7. The process according to claim 1, wherein the ratio of the ordered intermetallic compound and the inert material in the mixture is from 1:5 to 1:1000 by weight.

8. The process according to claim 1, wherein the mixture is obtained by a preparation method comprising the following steps:
   (1) melting together the metals constituting the ordered intermetallic compound to obtain a melt;
   (2) allowing the melt to cool down;
   (3) comminuting the melt obtained in step (2) to obtain a comminuted sample of the ordered intermetallic compound; and
   (4) mixing of the sample obtained in step (3) with the inert material.

9. The process according to claim 1, wherein the hydrogenation catalyst consists of the mixture.

10. The process according to claim 1, wherein the hydrogenation is a selective hydrogenation.

11. The process according to claim 1, wherein the unsaturated hydrocarbon compound has no hydrogenable group other than carbon-carbon double and/or carbon-carbon triple bonds.

12. The process according to claim 1, wherein the unsaturated hydrocarbon compound is selected from the group consisting of alkadienes, cycloalkadienes, alkynes and aryls.

13. The process according to claim 12, wherein the unsaturated hydrocarbon is ethyne which is converted to ethene through selective hydrogenation.

14. The process according to claim 13, wherein the ethyne is present in admixture with an excess of ethene, in the mixture to be reacted with hydrogen.

* * * * *